US012734117B2

(12) United States Patent
Fukada et al.

(10) Patent No.: US 12,734,117 B2
(45) Date of Patent: Sep. 15, 2026

(54) WATER-IN-OIL EMULSION COMPOSITION

(71) Applicant: SHOWA DENKO K.K., Tokyo (JP)

(72) Inventors: Go Fukada, Tokyo (JP); Eiko Kato, Tokyo (JP); Naoko Ito, Tokyo (JP)

(73) Assignee: Resonac Corporation, Tokyo (JP)

(*) Notice: Subject to any disclaimer, the term of this patent is extended or adjusted under 35 U.S.C. 154(b) by 873 days.

(21) Appl. No.: 17/632,725

(22) PCT Filed: Aug. 4, 2020

(86) PCT No.: PCT/JP2020/029805
§ 371 (c)(1),
(2) Date: Feb. 3, 2022

(87) PCT Pub. No.: WO2021/025013
PCT Pub. Date: Feb. 11, 2021

(65) Prior Publication Data

US 2022/0280396 A1 Sep. 8, 2022

(30) Foreign Application Priority Data

Aug. 7, 2019 (JP) ................................ 2019-145509

(51) Int. Cl.
*A61K 8/06* (2006.01)
*A61K 8/19* (2006.01)
*A61K 8/26* (2006.01)
*A61K 8/67* (2006.01)
*A61K 8/73* (2006.01)
*A61Q 19/00* (2006.01)

(52) U.S. Cl.
CPC ................ *A61K 8/064* (2013.01); *A61K 8/19* (2013.01); *A61K 8/26* (2013.01); *A61K 8/676* (2013.01); *A61K 8/731* (2013.01); *A61Q 19/00* (2013.01)

(58) Field of Classification Search
CPC . A61K 8/064; A61K 8/19; A61K 8/26; A61K 8/676; A61K 8/731; A61K 2800/10; A61K 2800/48; A61K 8/922; A61K 8/73; A61Q 19/00
See application file for complete search history.

(56) References Cited

U.S. PATENT DOCUMENTS 5,849,834 A * 12/1998 Matsuzaki .............. A61K 8/06 526/240
6,468,512 B1 * 10/2002 Carmody .............. A61Q 15/00 424/68
2005/0118211 A1 * 6/2005 Nakamura ............ A61K 8/733 424/401
2006/0216254 A1 * 9/2006 Majmudar .......... A61K 36/605 424/758
2008/0253982 A1 * 10/2008 Shibayama ........... A61Q 19/02 514/99
2009/0068255 A1 * 3/2009 Yu .......................... A61P 35/00 424/59
2014/0294904 A1 * 10/2014 Glatter .................. A61Q 19/00 514/777
2016/0324749 A1 11/2016 Imoto et al.

FOREIGN PATENT DOCUMENTS

| | | | | |
|---|---|---|---|---|
| EP | 1 475 070 A1 | 11/2004 | | |
| EP | 2 052 715 A1 | 4/2009 | | |
| JP | 2001-097815 A | 4/2001 | | |
| JP | 2002-212028 A | 7/2002 | | |
| JP | 2004-339106 A | 12/2004 | | |
| JP | 2007-204399 A | 8/2007 | | |
| JP | 2009-286735 A | 12/2009 | | |
| JP | 2013-216640 A | 10/2013 | | |
| TW | I650140 B | 2/2019 | | |
| WO | WO-9949878 A1 * | 10/1999 | ............. | A61P 17/00 |

OTHER PUBLICATIONS

Becker et. al. Safety Assessment of Ammonium Hectorites as Used in Cosmetics. International Journal of Toxicology 32(Supplement 4) 33S-40S. (Year: 2013).*
Becker . "Safety Assessment of Ammonium Hectorites as Used in Cosmetics" International Journal of Toxicology, 2013,32(Supplement 4) 33S-40S. (Year: 2013).*
INCIDecoder. "The Ordinary Magnesium Ascorbyl Phosphate 10%", 2016. (Year: 2016).*
PubChem. "Caprylyl laurate", 2025. (Year: 2025).*
Bellanoir Beauty "The Ordinary Magnesium Ascorbyl Phosphate 10%", 2017. (Year: 2017).*
Office Action issued from Taiwanese Patent Application No. 109126460 issued on Jun. 7, 2021.
International Search Report for PCT/JP2020/029805 dated Oct. 13, 2020 (PCT/ISA/210).

* cited by examiner

*Primary Examiner* — Sean M Basquill
*Assistant Examiner* — Rajan Pragani
(74) *Attorney, Agent, or Firm* — Sughrue Mion, PLLC

(57) ABSTRACT

A water-in-oil emulsion composition includes (a) at least one ascorbic acid phosphate ester compound selected from the group consisting of ascorbic acid phosphate esters and salts thereof, (b) an organically modified clay mineral, (c) an oil-based agent, and (d) water, in which a content of the component (b) is 0.2% by mass to 4.5% by mass.

10 Claims, No Drawings

WATER-IN-OIL EMULSION COMPOSITION

CROSS REFERENCE TO RELATED APPLICATIONS

This application is a National Stage of International Application No. PCT/JP2020/029805 filed Aug. 4, 2020, claiming priority based on Japanese Patent Application No. 2019-145509, filed Aug. 7, 2019, the contents of which are incorporated herein by reference.

TECHNICAL FIELD

The present invention relates to a water-in-oil emulsion composition.

BACKGROUND ART

Ascorbic acid phosphate esters and salts thereof promote collagen synthesis by being transferred to skin and converted to ascorbic acid. In addition, ascorbic acid phosphate esters and salts thereof suppress the degradation of collagen by inhibiting the activity of matrix metalloproteinases (MMPs). Due to these functions, ascorbic acid phosphate esters and salts thereof serve a very useful purpose with respect to skin. Therefore, ascorbic acid phosphate esters and salts thereof are components which are widely used in topical skin care products such as cosmetics; however, the above are unstable in aqueous solutions and, in particular, when blended in high concentrations, problems such as crystal precipitation and discoloration occur easily.

For this reason, methods for blending ascorbic acid derivatives in the aqueous phase of water-in-oil emulsion compositions have been tried. For example, Patent Document 1 describes a water-in-oil emulsion composition containing a partially cross-linked polyether-modified organopolysiloxane polymer, silicone oil, ascorbic acid, and water. Patent Document 2 describes a water-in-oil emulsion composition containing an ascorbic acid derivative, liquid cyclic dimethylpolysiloxane, polysaccharide fatty acid esters, and water. In many such water-in-oil emulsion compositions in which ascorbic acid derivatives are blended at high concentrations, the oil-based component is limited to silicone oil.

In addition, various thickening agents have been selected for the purpose of imparting high viscosity to water-in-oil emulsion compositions. However, in a case where ionic thickening agents are used in systems in which ascorbic acid derivatives are blended, decreases in viscosity occur due to the influence of electrolytes. On the other hand, even in a case where a non-ionic thickening agent, which is not easily influenced by electrolytes, is used, it is not possible to expect a high thickening effect and the contribution to the stability of the formulation is not sufficient.

CITATION LIST

Patent Documents

Patent Document 1

Japanese Unexamined Patent Application, First Publication No. 2004-339106

Patent Document 2

Japanese Unexamined Patent Application, First Publication No. 2007-204399

SUMMARY OF INVENTION

Technical Problem

As described above, water-in-oil emulsion compositions in which ascorbic acid derivatives were blended were not sufficiently stable in emulsification, as the crystals of the ascorbic acid derivatives in the composition precipitate over time, or the like. In particular, this problem was remarkable in a case where the water-in-oil emulsion composition contained a high concentration of ascorbic acid derivatives.

Therefore, the present invention has an object of providing a water-in-oil emulsion composition containing an ascorbic acid phosphate ester and/or salt thereof, which is able to suppress crystal precipitation over time.

Solution to Problem

The present invention includes the following aspects.

[1] A water-in-oil emulsion composition including (a) at least one ascorbic acid phosphate ester compound selected from the group consisting of ascorbic acid phosphate esters and salts thereof, (b) an organically modified clay mineral, (c) an oil-based agent, and (d) water, in which a content of the component (b) is 0.2% by mass to 4.5% by mass.

[2] The water-in-oil emulsion composition according to [1], in which the component (a) is a magnesium salt of the ascorbic acid phosphate ester.

[3] The water-in-oil emulsion composition according to [1] or [2], in which a content of the component (a) is 0.5% by mass to 20% by mass.

[4] The water-in-oil emulsion composition according to any one of [1] to [3], further including (e) at least one thickening agent selected from the group consisting of natural polymers and cellulose-based polymers.

[5] The water-in-oil emulsion composition according to [4], in which the component (e) is xanthan gum, gellan gum, or hydroxyethyl cellulose.

[6] The water-in-oil emulsion composition according to [4] or [5], in which a content of the component (e) is 0.01% by mass to 1% by mass.

[7] The water-in-oil emulsion composition according to any one of [1] to [6], in which the component (b) is organically modified hectorite.

[8] The water-in-oil emulsion composition according to [7], in which the organically modified hectorite is disteardimonium hectorite or quaternium-18 hectorite.

[9] The water-in-oil emulsion composition according to any one of [1] to [8], in which a content of the component (d) is 50% by mass to 90% by mass.

[10] The water-in-oil emulsion composition according to any one of [1] to [9], in which a mass ratio of the component (c) to the component (d) is (c):(d)=1:2 to 1:10.

[11] The water-in-oil emulsion composition according to any one of [1] to [10], in which a viscosity measured at 25° C. is 9 Pa·s to 50 Pa·s.

[12] The water-in-oil emulsion composition according to any one of [1] to [11], in which the water-in-oil emulsion composition is a cosmetic.

Advantageous Effects of Invention

The present invention provides a water-in-oil emulsion composition containing an ascorbic acid phosphate ester and/or salt thereof as active components, which is able to suppress crystal precipitation over time. In addition, there is provided a water-in-oil emulsion composition having excellent emulsion stability even when containing a high concentration of an ascorbic acid phosphate ester and/or salt thereof.

DESCRIPTION OF EMBODIMENTS

In one embodiment, the present invention provides a water-in-oil emulsion composition. The water-in-oil emulsion composition of the present embodiment contains at least the following components (a) to (d). In addition, the content of the component (b) described below is 0.2% by mass to 4.5% by mass with respect to the total mass (100% by mass) of the water-in-oil emulsion composition.

(a) At least one ascorbic acid phosphate ester compound selected from the group consisting of ascorbic acid phosphate esters and salts thereof
(b) Organically modified clay mineral
(c) Oil-based agent
(d) Water In the present specification, "water-in-oil emulsion composition" refers to an emulsion composition, in which the dispersed phase (the phase dispersed as droplets) is formed of water and the continuous phase (the outer phase) is formed of oil, and is also referred to as a water-in-oil emulsion (w/o type emulsion). It is possible to suitably use the water-in-oil emulsion composition as a formulation for cosmetics and the like.

[Component (a)]

The component (a) is at least one selected from the group consisting of ascorbic acid phosphate esters and salts thereof. Ascorbic acid phosphate esters are compounds in which a phosphate group is introduced into the hydroxy group of ascorbic acid. Ascorbic acid phosphate esters and salts thereof are confirmed to exhibit excellent functions with respect to skin, such as whitening effects, active oxygen removal effects, and an effect of improving skin damage such as spots, wounds, and burns. Therefore, blending ascorbic acid phosphate esters and/or salts thereof makes it possible to impart the above effects to water-in-oil emulsion compositions.

Examples of the ascorbic acid phosphate ester in component (a) include a compound represented by General Formula (1). The compound represented by General Formula (1) is an ascorbic acid-2-phosphate ester in which the hydroxyl group at the 2-position of the ascorbic acid is protected by a phosphate ester.

(1)

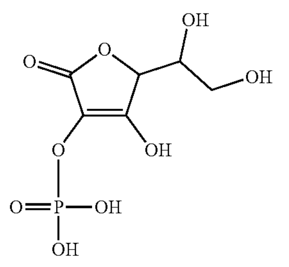

Ascorbic acid phosphate esters exist in D form, L form, and DL form. The ascorbic acid phosphate ester in the component (a) may be any of these stereoisomers, but is preferably the L form.

The salt of the ascorbic acid phosphate ester in component (a) is not particularly limited and examples thereof include a salt with an inorganic base, a salt with an organic base, and the like.

Examples of salts with an inorganic base include alkali metal salts such as sodium salts and potassium salts; alkaline earth metal salts such as calcium salts and magnesium salts; aluminum salts; ammonium salts; zinc salts, and the like.

Examples of salts with organic bases include alkylammonium salts, salts with basic amino acids, and the like.

Among the above, as the salt of ascorbic acid phosphate ester in the component (a), alkali metal salt or alkaline earth metal salt is preferable, sodium salt or magnesium salt is more preferable, and magnesium salt is even more preferable. The magnesium salt of ascorbic acid phosphate ester has advantages such as high stability and not coloring easily.

Examples of preferable forms of ascorbic acid phosphate ester in the component (a) include alkali metal salts (for example, sodium salts) of the compound represented by General Formula (1), alkaline earth metal salts (for example, magnesium salts) of the compound represented by General Formula (1), and the like.

A sodium salt of L-ascorbic acid-2-phosphate ester is commercially available from Showa Denko K.K. under the product name of Ascorbic acid PS (display name: sodium ascorbyl phosphate).

A magnesium salt of L-ascorbic acid-2-phosphate ester is commercially available from Showa Denko K.K. under the product name Ascorbic acid PM (display name: magnesium ascorbyl phosphate).

Ascorbic acid PS and Ascorbic acid PM are preferable examples of the component (a).

As the component (a), one selected from the group consisting of ascorbic acid phosphate esters and salts thereof may be used alone or two or more may be used in a combination. The component (a) preferably includes a salt of ascorbic acid phosphate ester and it is more preferable to use an alkali metal salt (for example, sodium salt) or an alkaline earth metal salt (for example, magnesium salt) of the ascorbic acid phosphate ester alone.

The content of the component (a) in the water-in-oil emulsion composition of the present embodiment is not particularly limited, but 0.5% by mass to 20% by mass with respect to the total mass (100% by mass) of the water-in-oil emulsion composition is preferable. When the content of the component (a) is 0.5% by mass or more, the functions of ascorbic acid phosphate ester or salt thereof (whitening effect, active oxygen removal effect, and the like) are more easily exhibited. In addition, when the content of the component (a) is 20% by mass or less, it is easier to obtain a balance with the other components. In a case where two or more selected from the group consisting of ascorbic acid phosphate esters and salts thereof are contained as the component (a), the content of the component (a) refers to the total content thereof.

The content of the component (a) in the water-in-oil emulsion composition of the present embodiment is more preferably 1% by mass to 18% by mass, even more preferably 2% by mass to 15% by mass, and particularly preferably 3% by mass to 12% by mass. In addition, as shown in the Examples below, it is also possible to set the content of the component (a) in the water-in-oil emulsion composition of the present embodiment to 5% by mass or more, to 7% by mass or more, or to 9% by mass or more.

In the formulations of the related art, when ascorbic acid phosphate ester and/or salts thereof were blended in high concentrations (for example, 3% by mass or more), there were problems such as crystals thereof precipitating during storage and attaching to the lid or rim of the container. On the other hand, in the water-in-oil emulsion composition of the present embodiment, even when ascorbic acid phosphate esters and/or salts thereof are blended at a high concentration (for example, 3% by mass or more), it is possible to suppress the precipitation of the crystals thereof and to maintain excellent emulsion stability.

It is possible to manufacture ascorbic acid phosphate esters or salts thereof by known manufacturing methods, for example, the methods described in Japanese Unexamined Patent Application, First Publication No. H2-279690, Japanese Unexamined Patent Application, First Publication No. H6-345786, and the like.

For example, it is possible to obtain the above by reacting ascorbic acid with phosphorus oxychloride or the like to carry out phosphorylation. Furthermore, it is possible to obtain a salt of an ascorbic acid phosphate ester by neutralizing the obtained ascorbic acid phosphate ester with a metal oxide such as magnesium oxide, a metal hydroxide such as sodium hydroxide, or the like.

[Component (b)]

The component (b) is an organically modified clay mineral. It is possible to obtain a stable emulsion state by blending the component (b). In the water-in-oil emulsion composition of the present embodiment, it is presumed that, by gelatinizing the oil phase, which is the continuous phase (outer phase), and suppressing the coalescence of the aqueous phase, which is the dispersed phase, it is possible for the organically modified clay mineral to maintain a stable emulsion state.

Organically modified clay minerals are minerals in which the converting cations intercalated between the crystalline layers of water-swelling clay minerals (for example, montmorillonite, saponite, hectorite, bentonite, and the like) are substituted with organic cationic compounds (for example, cationic surfactants such as quaternary ammonium salts).

The organically modified clay mineral to be blended in the water-in-oil emulsion composition of the present embodiment is not particularly limited beyond being a component generally used in cosmetics or the like. As organically modified clay minerals, it is possible to use minerals in which clay minerals such as montmorillonite, saponite, hectorite, bentonite, beidellite, nontronite, vermiculite, and laponite are treated with cationic surfactants such as quaternary ammonium salts.

Examples of quaternary ammonium salts used in the organic modification treatment of clay minerals include alkyltrimethylammonium chloride (for example, stearyltrimethylammonium chloride), dialkyldimethylammonium chloride (for example, distearyldimethylammonium chloride), benzalkonium chloride (for example, stearyldimethylbenzylammonium chloride), and the like.

Specific examples of organically modified clay minerals include organically modified hectorite such as disteardimonium hectorite, quaternium-18 hectorite, stearalkonium hectorite; organically modified bentonite such as quaternium-18 bentonite; and the like, but it is preferable to use organically modified hectorite.

Among the above, from the viewpoint of affinity with the oil-based agents described below, it is preferable to use disteardimonium hectorite or quaternium-18 hectorite and it is more preferable to use disteardimonium hectorite.

It is possible to use commercially available organically modified clay minerals without particular limitation. The organically modified clay minerals may be used as a premixed product dissolved in oil.

Commercially available products containing disteardimonium hectorite include NIKKOL (registered trademark) Nikkomulese (registered trademark) WO, NIKKOL Nikkomulese WO-CF, NIKKOL Nikkomulese WO-CF PLUS, NIKKOL Nikkomulese WO-NS (all manufactured by Nikko Chemicals Co., Ltd.), and the like. Examples of commercially available products of quaternium-18 hectorite include Sumecton (registered trademark)-SAN, Sumecton-SAN-P (both manufactured by Kunimine Industries, Ltd.), and the like.

One organically modified clay mineral may be used alone or two or more may be used in combination.

The content of the component (b) in the water-in-oil emulsion composition of the present embodiment is 0.2% by mass to 4.5% by mass with respect to the total mass (100% by mass) of the water-in-oil emulsion composition. The content of the component (b) being 0.2% by mass or more suppresses precipitation of crystals of the ascorbic acid phosphate ester and/or salt thereof and makes it possible to maintain a stable emulsion state. The content of the component (b) being 4.5% by mass or less makes it easy to obtain a balance with the other components and makes it possible to produce the water-in-oil emulsion composition.

The content of the component (b) in the water-in-oil emulsion composition of the present embodiment is preferably 0.3% by mass to 3.5% by mass, more preferably 0.4% by mass to 2.5% by mass, and even more preferably 0.5% by mass to 1.5% by mass.

[Component (c)]

The component (c) is an oil-based agent. The component (c) forms the oil phase in the water-in-oil emulsion composition of the present embodiment. The oil-based agent is a so-called oil (oil-based substance) and forms the water-in-oil emulsion together with the water of the component (d). In addition, by the oil-based agent, which is the component (c), being contained, the use feeling of the formulation, such as a cosmetic, is more desirable.

The type of oil-based agent is not particularly limited and, for example, it is possible to use silicone oil, ester oil, vegetable oil, hydrocarbon oil, and the like. One oil-based agent may be used alone or two or more may be used in combination.

The water-in-oil emulsion composition of the present embodiment preferably includes ester oil, vegetable oil, and hydrocarbon oil as oil-based agents. It is possible to set the blending ratio of these oil-based agents as appropriate according to the desired use feeling. Examples of the blending amount of silicone oil in the component (c) include 1% by mass to 20% by mass, 3% by mass to 15% by mass, 5% by mass to 12% by mass, or the like, with respect to the total mass (100% by mass) of the component (c). Examples of the blending amount of ester oil in the component (c) include 40% by mass to 75% by mass, 50% by mass to 70% by mass, 55% by mass to 65% by mass, or the like, with respect to the total mass (100% by mass) of the component (c). Examples of the blending amount of vegetable oil in the component (c) include 1% by mass to 20% by mass, 3% by mass to 15% by mass, 5% by mass to 13% by mass, or the like, with respect to the total mass (100% by mass) of the component (c). Examples of the blending amount of hydrocarbon oil in the component (c) includes 10% by mass to 40% by mass, 15% by mass to 35% by mass, 20% by mass to 30% by mass, or the like, with respect to the total mass (100% by mass) of the component (c).

In the related art, in a water-in-oil emulsion composition containing an ascorbic acid phosphate ester and/or salt thereof, the type of oil-based agent able to be blended was often limited to silicone oil. In the water-in-oil emulsion composition of the present embodiment, the type of oil-based agent is not limited to silicone oil and, depending on the application of the formulation and the desired use feeling of the formulation, it is possible to blend silicone oil, ester oil, vegetable oil, hydrocarbon oil, and the like in appropriate combinations.

Specific examples of silicone oils include dimethylpolysiloxane (dimethicone), cyclopentasiloxane, methylphenylpolysiloxane, methylhydrogenpolysiloxane, octamethylcyclotetrasiloxane, decamethylcyclopentasiloxane, dodecamethylcyclohexasiloxane, tetramethyltetrahydrogencyclotetrasiloxane, stearoxysilicone, and the like. Among these, dimethylpolysiloxane or cyclopentasiloxane is preferable since it is possible to obtain a relatively light feel as a formulation such as a cosmetic. As silicone oils, it is possible to use commercially available products without particular limitation.

Specific examples of ester oils include isodecyl neopentanoate, isocetyl octanoate, isononyl isononanoate, isodecyl isononanoate, tridecyl isononanoate, hexyl laurate, 2-hexyldecyl laurate, caprylyl laurate, isopropyl myristate, isocetyl myristate, isotridecyl myristate, 2-octyldodecyl myristate, isopropyl palmitate, 2-ethylhexyl palmitate, isooctyl palmitate, isocetyl palmitate, isodecyl palmitate, isostearyl palmitate, 2-octyldecyl palmitate, isopropyl isostearate, 2-octyldodecyl stearate, isostearyl isostearate, 2-octyldodecyl erucate, and the like. Among the above, isodecyl neopentanoate or caprylyl laurate is preferably used since it is possible to obtain a relatively light feel as a formulation such as a cosmetic. As ester oils, it is possible to use commercially available products without particular limitation.

Specific examples of vegetable oils include coconut oil, palm oil, palm kernel oil, safflower oil, olive oil, castor oil, jojoba oil, avocado oil, sesame oil, tea oil, evening primrose oil, wheat germ oil, macadamia nut oil, almond oil, hazelnut oil, candlenut oil, rosehip oil, meadowfoam oil, persic oil, tea tree oil, mentha oil, corn oil, rapeseed oil, sunflower oil, wheat germ oil, linseed oil, cottonseed oil, soybean oil, peanut oil, rice kernel oil, cacao oil, shea oil, hydrogenated coconut oil, hydrogenated castor oil, hydrogenated jojoba oil, and the like. Among the above, it is preferable to use palm oil, olive oil, jojoba oil, avocado oil, macadamia nut oil, candlenut oil, or meadowfoam oil due to the easy availability thereof. As vegetable oils, it is possible to use commercially available products without particular limitation.

Specific examples of hydrocarbon oils include fluid paraffin, heavy fluid isoparaffin, light fluid isoparaffin, α-olefin oligomers, polyisobutene, hydrogenated polyisobutene, polybutene, squalane, olive-derived squalane, squalene, vaseline, solid paraffin, and the like. Among the above, squalane or fluid paraffin is preferably used since it is possible to obtain a relatively light feel as a formulation such as a cosmetic. As hydrocarbon oils, it is possible to use commercially available products without particular limitation.

In a case where ester oil, vegetable oil, and hydrocarbon oil are included as the component (c), specific examples of combinations include caprylyl laurate and isodecyl neopentanoate as ester oil; at least one selected from the group consisting of palm oil, olive oil, jojoba oil, avocado oil, macadamia nut oil, candlenut oil, and meadowfoam oil as vegetable oil (preferably candlenut oil); at least one selected from the group consisting of squalane and fluid paraffin as hydrocarbon oil (preferably squalane), and the like.

The content of the component (c) in the water-in-oil emulsion composition of the present embodiment is preferably 5% by mass to 30% by mass with respect to the total mass (100% by mass) of the water-in-oil emulsion composition. When the content of the component (c) is in the preferable range, it is easy to adjust the feel of the formulation such as a cosmetic. The content of the component (c) in the water-in-oil emulsion composition of the present embodiment is more preferably 10% by mass to 25% by mass, and even more preferably 10% by mass to 20% by mass.

In the water-in-oil emulsion composition of the present embodiment, the ratio (mass ratio) of the oil-based agent, which is the component (c), and the water, which is the component (d), is preferably (c):(d)=1:2 to 1:10, and more preferably (c):(d)=1:4 to 1:6. When the ratio of the component (c) to the component (d) is in the preferable range, the ratio of the dispersed phase to the continuous phase becomes appropriate and thus it is possible to efficiently increase the viscosity of the water-in-oil emulsion composition.

[Component (d)]

The component (d) is water. The water may be any water able to be used for cosmetics, such as purified water. The component (d) forms the aqueous phase in the water-in-oil emulsion composition of the present embodiment. In addition, the component (d) is also used as a solvent for dissolving or mixing the component (a) described above and other optional components described below.

The content of the component (d) is the remaining amount of the total amount of the components (a) to (c) described above and other optional components described below.

The content of the component (d) in the water-in-oil emulsion composition of the present embodiment is preferably 50% by mass to 90% by mass with respect to the total mass (100% by mass) of the water-in-oil emulsion composition. When the content of the component (d) is in the preferable range, it is easy to dissolve the water-soluble component. The content of the component (d) in the water-in-oil emulsion composition of the present embodiment is more preferably 55% by mass to 85% by mass, even more preferably 60% by mass to 80% by mass, and particularly preferably 65% by mass to 75% by mass.

[Other Components]

The water-in-oil emulsion composition of the present embodiment may include other components as optional components in addition to the components (a) to (d) described above. Examples of the other components include a thickening agent, a surfactant, an emulsification aid, a preservative, and the like.

(Thickening Agent: Component (e))

The water-in-oil emulsion composition of the present embodiment preferably contains at least one thickening agent (referred to below as “component (e)”) selected from the group consisting of natural polymers and cellulose-based polymers. When the component (e) is blended in the water-in-oil emulsion composition of the present embodiment, it is possible to obtain a more stable emulsion state, which is preferable. It is presumed that the component (e) contributes to the stabilization of the emulsion state by increasing the viscosity of the aqueous phase, which is the dispersed phase.

Natural polymers are naturally existing polymers and examples thereof include polysaccharides, peptides, proteins, nucleic acids, and the like. As the natural polymers used as the component (e), polysaccharides, peptides, and proteins are preferable. Specific examples of natural polymers include xanthan gum, tamarind gum, locust bean gum, gellan gum, carrageenan, guar gum, gum arabic, agar, karaya gum, tragacanth gum, starch, alginic acid, alginate (for example, sodium alginate), dextran, dextrin, amylose, gelatin, collagen, pullulan, pectin, amylopectin, starch, chitin, albumin, casein, and the like. Among the above, since it is possible to expect a high thickening effect with a relatively small amount, xanthan gum, tamarind gum, locust bean gum, gellan gum, carrageenan, guar gum, gum arabic, agar, karaya gum, or tragacanth gum are preferable, and xanthan gum or gellan gum is more preferable.

Cellulose-based polymers are compounds in which some of the hydroxy groups of cellulose are substituted with other functional groups. Specific examples of cellulose-based polymers include methylcellulose, ethylcellulose, propylcellulose, ethylmethylcellulose, carboxymethylcellulose, hydroxyethylcellulose, hydroxypropylcellulose, hydroxypropylmethylcellulose, and the like. Among the above, due to being non-ionic, methylcellulose, ethylcellulose, propylcellulose, ethylmethylcellulose, hydroxyethylcellulose, hydroxypropylcellulose, or hydroxypropylmethylcellulose are preferable, and hydroxyethylcellulose is more preferable.

It is possible to use commercially available thickening agents without any limitation. Examples of commercially available xanthan gum include KELTROL (registered trademark) CG-SFT (manufactured by CP Kelco) and the like. Examples of commercially available products of gellan gum include KelcoGel (registered trademark) CG-LA (manufactured by CP Kelco) and the like. Examples of commercially available products of hydroxyethyl cellulose include HEC Daicel SE550 (manufactured by Daicel Finechem Ltd.) and the like.

One thickening agent selected from the group consisting of natural polymers and cellulose-based polymers may be used alone or two or more may be used together.

The content of the component (e) in the water-in-oil emulsion composition of the present embodiment is preferably 0.01% by mass to 1% by mass with respect to the total mass (100% by mass) of the water-in-oil emulsion composition. When the content of the component (e) is in the preferable range, it is possible to sufficiently increase the viscosity of the aqueous phase, which is the dispersed phase. The content of the component (e) in the water-in-oil emulsion composition of the present embodiment is more preferably 0.02% by mass to 0.8% by mass, and even more preferably 0.05% by mass to 0.5% by mass.

In a case where the component (e) is a natural polymer such as xanthan gum or gellan gum, when the content of the component (e) is 0.08% by mass to 0.5% by mass, yellowing of the water-in-oil emulsion composition is suppressed, which is particularly preferable.

In a case where the component (e) is a cellulose-based polymer such as hydroxyethyl cellulose, when the content of the component (e) is 0.12% by mass to 0.5% by mass, yellowing of the water-in-oil emulsion composition is suppressed, which is particularly preferable.

(Surfactant: Component (f))

The water-in-oil emulsion composition of the present embodiment preferably contains a surfactant (referred to below as "component (f)"). When the water-in-oil emulsion composition contains the component (f), it is possible for the organically modified clay mineral, which is the component (b), to form a complex with the component (f) and construct an oil gel.

The type of surfactant is not particularly limited and, for example, it is possible to use polyglycerin fatty acid esters, sorbitan fatty acid esters, sucrose fatty acid esters, and the like. Among the above, polyglycerin fatty acid esters are preferable since it is possible to increase the viscosity of the water-in-oil emulsion composition more efficiently with a small amount. One surfactant may be used alone or two or more may be used in combination.

Specific examples of polyglycerin fatty acid esters include polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, polyglyceryl-6 distearate, polyglyceryl-10 distearate, polyglyceryl-2 tristearate, polyglyceryl-10 decastearate, polyglyceryl-2 isostearate, polyglyceryl-3 isostearate, polyglyceryl-4 isostearate, polyglyceryl-5 isostearate, polyglyceryl-6 isostearate, polyglyceryl-8 isostearate, polyglyceryl-10 isostearate, polyglyceryl-2 diisostearate, polyglyceryl-3 diisostearate, polyglyceryl-10 diisostearate, polyglyceryl-2 triisostearate, polyglyceryl-2 tetraisostearate, polyglyceryl-10 decaisostearate, polyglyceryl-2 oleate, polyglyceryl-3 oleate, polyglyceryl-4 oleate, polyglyceryl-5 oleate, polyglyceryl-6 oleate, polyglyceryl-8 oleate, polyglyceryl-10 oleate, polyglyceryl-6 dioleate, polyglyceryl-2 trioleate, polyglyceryl-10 decaoleate, polyglyceryl-6 polyricinoleate, polyglyceryl-10 polyricinoleate, and the like. Among the above, polyglyceryl-2 isostearate or polyglyceryl-6 polyricinoleate is preferable since the balance of hydrophilic and lipophilic properties is appropriate.

As surfactants, it is possible to use commercially available products without particular limitation. When a premixed product is used in which the surfactant, which is the component (f), and the organically modified clay mineral, which is the component (b), are mixed in advance, it is easy to produce the formulation, which is preferable.

In a case where the water-in-oil emulsion composition of the present embodiment contains a surfactant, the content of the surfactant is preferably 1% by mass to 20% by mass with respect to the total mass (100% by mass) of the water-in-oil emulsion composition. When the content of the surfactant is in the preferable range, it becomes possible to more efficiently increase the viscosity of the water-in-oil emulsion composition in combination with the organically modified clay mineral, which is the component (b). The content of the surfactant in the water-in-oil emulsion composition of the present embodiment is more preferably 2% by mass to 15% by mass, and even more preferably 3% by mass to 10% by mass.

(Emulsification Aid: Component (g))

The water-in-oil emulsion composition of the present embodiment preferably contains an emulsification aid (referred to below as "component (g)"). When the water-in-oil emulsion composition contains an emulsification aid, it is possible to further increase the stability of the water-in-oil emulsion composition.

Specific examples of emulsification aids include sodium chloride, magnesium sulfate, and the like. Among the above, it is preferable to use magnesium sulfate as an emulsification aid since the use feeling is superior.

In a case where the water-in-oil emulsion composition of the present embodiment contains an emulsification aid, the content of the emulsification aid is preferably 0.1% by mass to 5% by mass with respect to the total mass (100% by mass) of the water-in-oil emulsion composition. When the content of the emulsification aid is in the preferable range, it is possible to suppress the content of the surfactant, which is the component (f), and to perform emulsification more efficiently. The content of the emulsification aid in the water-in-oil emulsion composition of the present embodiment is preferably 0.5% by mass to 3% by mass.

(Preservative: Component (h))

The water-in-oil emulsion composition of the present embodiment preferably contains a preservative (referred to below as "component (h)"). When the water-in-oil emulsion composition contains a preservative, it is possible to prevent deterioration of the components in the composition.

Specific examples of preservatives include phenoxyethanol, methylparaben, propylparaben, hydroxyacetophenone, and the like. Among the above, parabens such as methylparaben and propylparaben exhibit high antibacterial activity in small amounts and also exhibit antibacterial activity evenly and thoroughly against kinds of fungi, which is therefore preferable.

In a case where the water-in-oil emulsion composition of the present embodiment contains a preservative, depending on the type of the preservative, it is possible to set the content of the preservative, for example, to 0.1% by mass to 0.6% by mass with respect to the total mass (100% by mass) of the water-in-oil emulsion composition. In a case where the preservative is phenoxyethanol, the content is preferably 0.1% by mass to 0.6% by mass, and more preferably 0.2% by mass to 0.5% by mass. In a case where the preservative is methylparaben and/or propylparaben, the content is preferably 0.1% by mass to 0.5% by mass, and more preferably 0.2% by mass to 0.4% by mass. When the content of the preservative is in the preferable range, it is possible to exhibit sufficient antibacterial activity and suppress irritation of the skin.

(Other: Component (i))

It is possible for the water-in-oil emulsion composition of the present embodiment to contain, in addition to those listed above, any component (referred to below as "component (i)") generally used in cosmetics as long as the effect of the present invention is not impaired.

Examples of such components include antioxidants (for example, tocopherols), moisturizers (for example, glycerin), antibacterial agents, whitening agents, vitamins and derivatives thereof, inflammation preventing agents, anti-inflammatory agents, blood circulation accelerators, hormones, anti-wrinkle agents, anti-aging agents, finning agents, cooling agents, warming agents, wound healing accelerators, irritant relievers, analgesics, cell-stimulating agents, plant, animal, and microorganism extracts, antipruritic agents, keratin stripping and dissolving agents, astringents, enzymes, nucleic acids, fragrances, dyes, colorants, anti-inflammatory and analgesic agents, antifungal agents, antihistamines, antibiotics, antibacterial substances, herbal medicines, antipruritic drugs, keratin softening and stripping agents, antiseptic and bactericidal agents, additives, and the like. Specific examples of these components include those components described in Japanese Unexamined Patent Application, First Publication No. 2016-50196, for example. One other component may be used alone or two or more may be used in combination.

Manufacturing Method

It is possible to manufacture the water-in-oil emulsion composition of the present embodiment by mixing the components (a) to (d) described above and carrying out mixing by adding other optional components thereto. Specific examples of the method for manufacturing the water-in-oil emulsion composition of the present embodiment are illustrated below, without being limited thereto.

The component (a) is gradually added to water and dissolved to prepare an aqueous solution of the component (a). In addition, in a case where the component (e) is to be added, the component (e) is dissolved in water in advance to prepare an aqueous solution of the component (e). The other water-soluble components and the aqueous solution of component (e) prepared in advance are added to the aqueous solution of the component (a) at room temperature and dissolved to obtain an aqueous phase portion.

Next, the component (b) (preferably a premixed product with component (f)) is added at room temperature to a mixture in which the component (c) and other oil-based components are stirred until uniform. An oil phase portion is obtained by stirring the result until uniform.

The oil phase portion prepared by the procedure described above is stirred with an agitator such as a Homo Disper at room temperature and the aqueous phase portion is gradually added to the oil phase portion over approximately 10 minutes. Thereafter, it is possible to further obtain the water-in-oil emulsion composition by further stirring with a dispersing machine such as a Polytron (registered trademark) homogenizer for approximately 5 minutes.

The shape of the agitating blades of the Homo Disper is not particularly limited and, for example, it is possible to use a paddle type, anchor type, propeller type, or the like. The rotation speed of the Homo Disper is, for example, 600 rpm to 2000 rpm, and preferably 800 rpm to 1600 rpm.

The shape and size of the generator shaft of the polytron homogenizer are not particularly limited and it is possible to use commercially available products as appropriate. The rotation speed of the polytron homogenizer is, for example, 1000 rpm to 7000 rpm, and preferably 2000 rpm to 6000 rpm.

The viscosity at 25° C. of the produced water-in-oil emulsion composition is preferably 9 Pa·s to 50 Pa·s, and more preferably 12 Pa·s to 45 Pa·s. When the viscosity is in the preferable range, it is possible to maintain a more stable emulsion state. When the viscosity of the water-in-oil emulsion composition at 25° C. is 14 Pa·s to 40 Pa·s, it is possible to suppress yellowing of the water-in-oil emulsion composition, which is more preferable. The viscosity of the water-in-oil emulsion composition was measured using a B-type viscometer under the conditions described in the Examples below.

The water-in-oil emulsion composition of the present embodiment contains the components (a) to (d) described above and contains the component (b) in a specific content (0.2% by mass to 4.5% by mass) and, due to this, even in a case where a high concentration (for example, 3% by mass or more, 6% by mass or more, or 8% by mass or more) of an ascorbic acid phosphate ester and/or salt thereof is contained, the emulsion stability is excellent and the ascorbic acid phosphate ester and/or salt thereof do not easily precipitate. In addition, since it is possible to blend oil-based agents other than silicone oil as the oil-based agent, it is possible to adjust the desired use feeling according to the application of the formulation such as a cosmetic. In addition, further containing a thickening agent as the component (e) makes it possible to further improve stability and suppress yellowing.

EXAMPLES

A more detailed description will be given below of the present invention based on Examples below, but the present invention is not limited to these Examples.

In the Examples and Comparative Examples described below, ascorbic acid PM (referred to below as "ascorbyl magnesium phosphate") manufactured by Showa Denko K.K. was used as the component (a).

In addition, in Comparative Example 2, bentonite (Kunipia-G10, manufactured by Kunimine Industries, Ltd.), which was a clay mineral (referred to below as component (b')), was used instead of an organically modified clay mineral, which was the component (b).

The product names and the like of other components used in the Examples and Comparative Examples described below are shown below.

(e) Xanthan gum: KELTROL CG-SFT (manufactured by CP Kelco)

(e) Gellan gum: KELCOGEL CG-LA (manufactured by CP Kelco)

(e) Hydroxyethyl cellulose: HEC Daicel SE550 (manufactured by Daicel Finechem Ltd.)

(b) Disteardimonium hectorite (premixed product with (f) polyglyceryl-6 polyricinoleate and (f) polyglyceryl-2 isostearate): NIKKOL Nikkomulese WO-NS (manufactured by Nikko Chemicals Co., Ltd.)

(b) Quaternium-18 hectorite: Sumecton-SAN-P (manufactured by Kunimine Industries, Ltd.)

(c) Caprylyl laurate: NIKKOL GS-KL (manufactured by Nikko Chemicals Co., Ltd.)

(c) Isodecyl neopentanoate: Neolite 100P (manufactured by Kokyu Alcohol Kogyo Co., Ltd.)

(c) Candlenut oil: NIKKOL Candlenut oil (manufactured by Nikko Chemicals Co., Ltd.)

(c) Squalane: Squalane (manufactured by Kishimoto Special Liver Oil Industry Co., Ltd.)

Example 1

66.6 g of water was placed in a 100-mL beaker and dissolved by gradually adding 10 g of ascorbyl magnesium phosphate while stirring using a magnetic stirrer.

To the above, 1.0 g of glycerin, 1.0 g of magnesium sulfate, and 0.3 g of phenoxyethanol were added in order and dissolved until the solution became uniform, thereby obtaining an aqueous phase portion A.

Next, 6.0 g of caprylyl laurate, 3.0 g of isodecyl neopentanoate, 4.0 g of squalane, 1.0 g of candlenut oil, 1.0 g of dimethicone, and 0.1 g of tocopherol, which were oil-based components, were added to a 200-mL beaker and lightly stirred with a magnetic stirrer until uniform. Furthermore, 6.0 g of NIKKOL Nicomuls WO-NS (manufactured by Nikko Chemicals Co., Ltd.) was added thereto and an oil phase portion B was obtained by stirring until the paste-like portion was uniformly dispersed.

The oil phase portion B was stirred at 1000 rpm at room temperature using a Three-One Motor (registered trademark) FBL1200 (manufactured by Shinto Scientific Co., Ltd.) (agitating blade: DP80 with SUS disper 80 mm bosses) and the aqueous phase portion A was gradually added to the oil phase portion B over 10 minutes. Thereafter, a water-in-oil emulsion composition was obtained by further stirring the entire composition evenly and thoroughly at 3000 rpm for 5 minutes using a T 25 digital ULTRA-TURRAX (manufactured by IKA Japan Co., Ltd.) (shaft model no.: S25N-18G).

Examples 2 and 3

Water-in-oil emulsion compositions were produced by the same procedure as in Example 1, with the components and contents described in Table 1, respectively.

Example 4

A 2% aqueous solution of xanthan gum was prepared by uniformly dissolving 0.1 g of xanthan gum in 4.9 g of water in advance. 61.6 g of water was placed in a 100-mL beaker and 10 g of ascorbyl magnesium phosphate was gradually added thereto and dissolved while stirring using a magnetic stirrer. To the above, 1.0 g of glycerin, 1.0 g of magnesium sulfate, 0.3 g of phenoxyethanol, and 5.0 g of the aqueous solution of xanthan gum described above were added in order and dissolved until the solution became uniform to obtain the aqueous phase portion A.

Next, 6.0 g of caprylyl laurate, 3.0 g of isodecyl neopentanoate, 4.0 g of squalane, 1.0 g of candlenut oil, 1.0 g of dimethicone, and 0.1 g of tocopherol, which were oil-based components, were added to a 200-mL beaker and the mixture was lightly stirred with a magnetic stirrer until uniform. Furthermore, 6.0 g of NIKKOL Nicomuls WO-NS (manufactured by Nikko Chemicals Co., Ltd.) was added thereto and the oil phase portion B was obtained by stirring until the paste-like portion was uniformly dispersed.

While stirring the oil phase portion B at 1000 rpm using a Homo Disper at room temperature, the aqueous phase portion A was gradually added to the oil phase portion B over 10 minutes. Thereafter, the water-in-oil emulsion composition was obtained by further stirring the entire composition evenly and thoroughly at 3000 rpm for 5 minutes using a Polytron homogenizer.

Examples 5 to 22, Comparative Examples 1 and 2

Water-in-oil emulsion compositions were prepared by the same procedure as in Example 4, with the components and contents described in Table 1 and Table 2, respectively.

Among the formulations shown in Tables 1 and 2, it was not possible to produce a water-in-oil emulsion composition with the formulation of Comparative Example 2.

Examples 23 to 25

Water-in-oil emulsion compositions were produced by the same procedure as in Example 4, with the components and contents described in Table 3, respectively. In Examples 23 to 25, a preservative (component (h)) was also added to the oil phase portion B.

NIKKOL Nicomuls WO-NS (manufactured by Nikko Chemicals Co., Ltd.), which is a premixed product, contains 10% by mass to 20% by mass of disteardimonium hectorite. Accordingly, for example, in a case where 0.5% by mass of the premixed product is added (Comparative Example 1), the content of disteardimonium hectorite in the water-in-oil emulsion composition is 0.05% by mass to 0.1% by mass, and in a case where 4.0% by mass of the premixed product is added (Example 20), the content of disteardimonium hectorite in the water-in-oil emulsion composition is 0.4% by mass to 0.8% by mass.

That is, the content of the component (b) is 0.2% by mass or more in Examples 1 to 25 and less than 0.2% by mass in Comparative Example 1.

TABLE 1

| | | | Example 1 | Example 2 | Example 3 | Example 4 | Example 5 | Example 6 |
|---|---|---|---|---|---|---|---|---|
| Aqueous phase portion A | Component (a) | Ascorbyl magnesium phosphate | 10.00 | 10.00 | 10.00 | 10.00 | 8.00 | 6.00 |
| | Component (d) | Water | 66.60 | 64.60 | 62.60 | 66.50 | 68.50 | 69.50 |
| | Component (e) | Xanthan gum | | | | 0.10 | 0.10 | 0.10 |
| | | Gellan gum | | | | | | |
| | | Hydroxyethyl cellulose | | | | | | |
| | Component (g) | Magnesium sulfate | 1.00 | 1.00 | 1.00 | 1.00 | 1.00 | 1.00 |
| | | Sodium chloride | | | | | | |
| | Component (i) | Glycerin | 1.00 | 1.00 | 1.00 | 1.00 | 1.00 | 1.00 |
| | Component (h) | Phenoxyethanol | 0.30 | 0.30 | 0.30 | 0.30 | 0.30 | 0.30 |
| Oil phase portion B | Component (b') | Bentonite | | | | | | |
| | Component (b) | Quaternium-18 hectorite | | | | | | |
| | | Disteardimonium hectorite | 6.00 | 8.00 | 10.00 | 6.00 | 6.00 | 6.00 |
| | Component (f) | Polyglyceryl-2 isostearate | | | | | | |
| | | Polyglyceryl-6 polyricinoleate | | | | | | |
| | Component (c) | Caprilyl laurate | 6.00 | 6.00 | 6.00 | 6.00 | 6.00 | 6.00 |
| | | Isodecyl neopentaneate | 3.00 | 3.00 | 3.00 | 3.00 | 3.00 | 3.00 |
| | | Squalene | 4.00 | 4.00 | 4.00 | 4.00 | 4.00 | 4.00 |
| | | Candlenut oil | 1.00 | 1.00 | 1.00 | 1.00 | 1.00 | 2.00 |
| | | Dimethicone | 1.00 | 1.00 | 1.00 | 1.00 | 1.00 | 1.00 |
| | Component (i) | Tocopherol | 0.10 | 0.10 | 0.10 | 0.10 | 0.10 | 0.10 |
| Was a formulation prepared? | | | ○ | ○ | ○ | ○ | ○ | ○ |
| Viscosity at 12 rpm (mPa · s) | | | 10,550 | 14,210 | 18,770 | 15,230 | 15,220 | 15,670 |
| Stability evaluation test 1 | | Presence or absence of crystal precipitation | A | A | A | A | A | A |
| Stability evaluation test 2 | | Presence or absence of separation | A | A | A | A | A | A |
| | | Presence or absence of yellowing | B | A | A | A | A | A |

| | | | Example 7 | Example 8 | Example 9 | Example 10 | Example 11 |
|---|---|---|---|---|---|---|---|
| Aqueous phase portion A | Component (a) | Ascorbyl magnesium phosphate | 3.00 | 10.00 | 10.00 | 10.00 | 10.00 |
| | Component (d) | Water | 71.50 | 66.58 | 66.54 | 66.46 | 66.42 |
| | Component (e) | Xanthan gum | 0.10 | 0.02 | 0.06 | 0.14 | 0.18 |
| | | Gellan gum | | | | | |
| | | Hydroxyethyl cellulose | | | | | |
| | Component (g) | Magnesium sulfate | 1.00 | 1.00 | 1.00 | 1.00 | 1.00 |
| | | Sodium chloride | | | | | |
| | Component (i) | Glycerin | 1.00 | 1.00 | 1.00 | 1.00 | 1.00 |
| | Component (h) | Phenoxyethanol | 0.30 | 0.30 | 0.30 | 0.30 | 0.30 |
| Oil phase portion B | Component (b') | Bentonite | | | | | |
| | Component (b) | Quaternium-18 hectorite | | | | | |
| | | Disteardimonium hectorite | 6.00 | 6.00 | 6.00 | 6.00 | 6.00 |
| | Component (f) | Polyglyceryl-2 isostearate | | | | | |
| | | Polyglyceryl-6 polyricinoleate | | | | | |
| | Component (c) | Caprilyl laurate | 6.00 | 6.00 | 6.00 | 6.00 | 6.00 |
| | | Isodecyl neopentaneate | 3.00 | 3.00 | 3.00 | 3.00 | 3.00 |
| | | Squalene | 4.00 | 4.00 | 4.00 | 4.00 | 4.00 |
| | | Candlenut oil | 2.00 | 1.00 | 1.00 | 1.00 | 1.00 |
| | | Dimethicone | 2.00 | 1.00 | 1.00 | 1.00 | 1.00 |

TABLE 1-continued

| | | | | | | | |
|---|---|---|---|---|---|---|---|
| Component (i) | Tocopherol | 0.10 | 0.10 | 0.10 | 0.10 | 0.10 |
| Was a formulation prepared? | | ○ | ○ | ○ | ○ | ○ |
| Viscosity at 12 rpm (mPa · s) | | 16,320 | 11,110 | 13,890 | 16,540 | 19,240 |
| Stability evaluation test 1 | Presence or absence of crystal precipitation | A | A | A | A | A |
| Stability evaluation test 2 | Presence or absence of separation | A | A | A | A | A |
| | Presence or absence of yellowing | A | B | B | A | A |

TABLE 2

| | | | Example 12 | Example 13 | Example 14 | Example 15 | Example 16 | Example 17 | Example 18 |
|---|---|---|---|---|---|---|---|---|---|
| Aqueous phase portion A | Component (a) | Ascorbyl magnesium phosphate | 10.00 | 10.00 | 8.00 | 6.00 | 3.00 | 10.00 | 10.00 |
| | Component (d) | Water | 66.58 | 66.54 | 68.50 | 70.50 | 73.50 | 66.50 | 66.46 |
| | Component (e) | Xanthan gum | | | | | | | |
| | | Gellan gum | 0.02 | 0.06 | 0.10 | 0.10 | 0.10 | | |
| | | Hydroxyethyl cellulose | | | | | | 0.10 | 0.14 |
| | Component (g) | Magnesium sulfate | 1.00 | 1.00 | 1.00 | 1.00 | 1.00 | 1.00 | 1.00 |
| | | Sodium chloride | | | | | | | |
| | Component (i) | Glycerin | 1.00 | 1.00 | 1.00 | 1.00 | 1.00 | 1.00 | 1.00 |
| | Component (h) | Phenoxyethanol | 0.30 | 0.30 | 0.30 | 0.30 | 0.30 | 0.30 | 0.30 |
| Oil phase portion B | Component (b') | Bentonite | | | | | | | |
| | Component (b) | Quaternium-18 hectorite | | | | | | | |
| | | Disteardimonium hectorite | 6.00 | 6.00 | 6.00 | 6.00 | 6.00 | 6.00 | 6.00 |
| | Component (f) | Polyglyceryl-2 isostearate | | | | | | | |
| | | Polyglyceryl-6 polyricinoleate | | | | | | | |
| | Component (c) | Caprilyl laurate | 6.00 | 6.00 | 6.00 | 6.00 | 6.00 | 6.00 | 6.00 |
| | | Isodecyl neopentaneate | 3.00 | 3.00 | 3.00 | 3.00 | 3.00 | 3.00 | 3.00 |
| | | Squalene | 4.00 | 4.00 | 4.00 | 4.00 | 4.00 | 4.00 | 4.00 |
| | | Candlenut oil | 1.00 | 1.00 | 1.00 | 1.00 | 1.00 | 1.00 | 1.00 |
| | | Dimethicone | 1.00 | 1.00 | 1.00 | 1.00 | 1.00 | 1.00 | 1.00 |
| | Component (i) | Tocopherol | 0.10 | 0.10 | 0.10 | 0.10 | 0.10 | 0.10 | 0.10 |
| Was a formulation prepared? | | | ○ | ○ | ○ | ○ | ○ | ○ | ○ |
| Viscosity at 12 rpm (mPa · s) | | | 11,220 | 13,220 | 15,120 | 16,230 | 17,210 | 13,000 | 14,770 |
| Stability evaluation test 1 | | Presence or absence of crystal precipitation | A | A | A | A | A | A | A |
| Stability evaluation test 2 | | Presence or absence of separation | A | A | A | A | A | A | A |
| | | Presence or absence of yellowing | B | B | A | A | A | B | A |

| | | | Example 19 | Comparative example 1 | Example 20 | Example 21 | Comparative example 2 | Example 22 |
|---|---|---|---|---|---|---|---|---|
| Aqueous phase portion A | Component (a) | Ascorbyl magnesium phosphate | 10.00 | 10.00 | 10.00 | 10.00 | 10.00 | 10.00 |
| | Component (d) | Water | 66.42 | 72.00 | 68.50 | 66.50 | 66.50 | 66.50 |
| | Component (e) | Xanthan gum | | 0.10 | 0.10 | 0.10 | 0.10 | 0.10 |
| | | Gellan gum | | | | | | |
| | | Hydroxyethyl cellulose | 0.18 | | | | | |
| | Component (g) | Magnesium sulfate | 1.00 | 1.00 | 1.00 | 1.00 | 1.00 | |
| | | Sodium chloride | | | | | | 1.00 |
| | Component (i) | Glycerin | 1.00 | 1.00 | 1.00 | 1.00 | 1.00 | 1.00 |
| | Component (h) | Phenoxyethanol | 0.30 | 0.30 | 0.30 | 0.30 | 0.30 | 0.30 |

TABLE 2-continued

| | | | | | | | | |
|---|---|---|---|---|---|---|---|---|
| Oil phase portion B | Component (b') | Bentonite | | | | | 0.90 | |
| | Component (b) | Quaternium-18 hectorite | | | | 0.90 | | |
| | | Disteardimonium hectorite | 6.00 | 0.50 | 4.00 | | | 6.00 |
| | Component (f) | Polyglyceryl-2 isostearate | | | | 1.40 | 1.40 | |
| | | Polyglyceryl-6 polyricinoleate | | | | 3.70 | 3.70 | |
| | Component (c) | Caprilyl laurate | 6.00 | 6.00 | 6.00 | 6.00 | 6.00 | 6.00 |
| | | Isodecyl neopentaneate | 3.00 | 3.00 | 3.00 | 3.00 | 3.00 | 3.00 |
| | | Squalene | 4.00 | 4.00 | 4.00 | 4.00 | 4.00 | 4.00 |
| | | Candlenut oil | 1.00 | 1.00 | 1.00 | 1.00 | 1.00 | 1.00 |
| | | Dimethicone | 1.00 | 1.00 | 1.00 | 1.00 | 1.00 | 1.00 |
| | Component (i) | Tocopherol | 0.10 | 0.10 | 0.10 | 0.10 | 0.10 | 0.10 |
| Was a formulation prepared? | | | ○ | ○ | ○ | ○ | X | ○ |
| Viscosity at 12 rpm (mPa · s) | | | 16,980 | 1,280 | 9,012 | 15,110 | — | 15,220 |
| Stability evaluation test 1 | | Presence or absence of crystal precipitation | A | B | A | A | — | A |
| Stability evaluation test 2 | | Presence or absence of separation | A | B | A | A | — | A |
| | | Presence or absence of yellowing | A | B | B | A | — | A |

TABLE 3

| | | | Example 23 | Example 24 | Example 25 |
|---|---|---|---|---|---|
| Aqueous phase portion A | Component (a) | Ascorbyl magnesium phosphate | 6.00 | 3.00 | 10.00 |
| | Component (d) | Water | 70.55 | 73.55 | 66.55 |
| | Component (e) | Xanthan gum | 0.10 | 0.10 | 0.10 |
| | | Gellan gum | | | |
| | | Hydroxyethyl cellulose | | | |
| | Component (g) | Magnesium sulfate | 1.00 | 1.00 | 1.00 |
| | | Sodium chloride | | | |
| | Component (i) | Glycerin | 1.00 | 1.00 | 1.00 |
| | Component (h) | Phenoxyethanol | | | |
| | | Methylparaben | 0.20 | 0.20 | 0.15 |
| Oil phase portion B | Component (b') | Bentonite | | | |
| | Component (b) | Quaternium-18 hectorite | | | |
| | | Disteardimonium hectorite | 6.00 | 6.00 | 6.00 |
| | Component (f) | Polyglyceryl-2 isostearate | | | |
| | | Polyglyceryl-6 polyricinoleate | | | |
| | Component (c) | Caprilyl laurate | 6.00 | 6.00 | 6.00 |
| | | Isodecyl neopentaneate | 3.00 | 3.00 | 3.00 |
| | | Squalene | 4.00 | 4.00 | 4.00 |
| | | Candlenut oil | 1.00 | 1.00 | 1.00 |
| | | Dimethicone | 1.00 | 1.00 | 1.00 |
| | Component (i) | Tocopherol | 0.10 | 0.10 | 0.10 |
| | Component (h) | Methylparaben | | | 0.05 |
| | | Propylparaben | 0.05 | 0.05 | 0.05 |
| Was a formulation prepared? | | | ○ | ○ | ○ |
| Viscosity at 12 rpm (mPa · s) | | | 15,430 | 15,120 | 15,220 |
| Stability evaluation test 1 | | Presence or absence of crystal precipitation | A | A | A |
| Stability evaluation test 2 | | Presence or absence of separation | A | A | A |
| | | Presence or absence of yellowing | A | A | A |

[Measurement of Viscosity]

The viscosity of the produced water-in-oil emulsion composition at 25° C. was measured using a B-type viscometer LVDV2T (manufactured by EKO Instruments Co., Ltd.) and an RV-2 spindle as the spindle size. The measurement results at 12 rpm are shown in Tables 1 to 3.

[Stability Evaluation Test 1]

The produced water-in-oil emulsion compositions (referred to below as "samples") were evaluated for stability over time based on the presence or absence of crystal precipitation.

A plastic wrap was prepared and placed horizontally on a desk and both the left and right sides were fixed to the desk with duct tape. Square areas of 1.5 cm in length and width were set up thereon in a horizontal row for the number of samples. 0.2 g of the samples was coated evenly on each area. An iron bar wrapped once with a plastic wrap was prepared and used to spread the samples evenly lengthwise to 15 cm. Thereafter, a dryer was used to blow air (at approximately 25° C.) evenly and thoroughly over the samples for 30 seconds. A 30-second air blowing treatment was set as one set and the state of the samples was confirmed after each set finished. This operation was repeated for 10 sets.

The results are shown in Table 1 to Table 3. The presence or absence of crystal precipitation in the samples was evaluated based on the following criteria.

Presence or Absence of Crystal Precipitation

A: There was no crystal precipitation even at the end of 10 sets.

B: Crystal precipitation was observed by the end of 4 sets.

In Comparative Example 1, crystal precipitation was observed in the system at the end of 4 sets and the number of crystals increased as the air blowing treatment continued. Since the content of the organically modified clay mineral was low in Comparative Example 1, it is considered that it was not possible to sufficiently gelatinize the oil phase, which coalesced with the aqueous phase, resulting in the precipitation of crystals of ascorbyl magnesium phosphate.

On the other hand, in Examples 1 to 25, no crystal precipitation was observed even at the end of 10 sets. In this manner, it was confirmed that Examples 1 to 25 were water-in-oil emulsion compositions with excellent emulsion stability, in which crystal precipitation over time was suppressed.

[Stability Evaluation Test 2]

The produced water-in-oil emulsion compositions (referred to below as "samples") were subjected to an acceleration test at 50° C. and the stability over time was evaluated based on the separation and yellowing of the samples.

30-mL vials were prepared as a number of samples and each was filled with each sample to a height of 4 cm from the bottom. After filling, the lids were closed and the vials were stored at 50° C. in an air atmosphere. After one month, each sample was observed for the presence or absence of separation and yellowing.

The results are shown in Tables 1 to 3. The presence or absence of separation of the samples and the presence or absence of yellowing were evaluated according to the following criteria.

Presence or Absence of Separation

A: No phase separation was observed.

B: Phase separation was observed.

Presence or Absence of Yellowing

A: No yellowing was observed, and the color remained milky white.

B: Yellowing was observed.

For Examples 1, 8, 9, 12, 13, 17, 20, and Comparative Example 1, in which yellowing was observed as described above, small amounts of samples were taken from the lower part (0 cm to less than 1.3 cm from the bottom), middle part (1.3 cm to less than 2.6 cm from the bottom), and upper part (2.6 cm to 4.0 cm from the bottom) of each sample vial, respectively, and the color change of the samples was evaluated by the Munsell color system using a color scheme sample (Japan Paint Manufacturers' Association Color Sample Book, Standard Colors for Paints, 2019 K Edition, Pocket Edition).

The results are shown in Table 4.

TABLE 4

| | | | Example 1 | Example 8 | Example 9 | Example 12 | Example 13 | Example 17 | Comparative example 1 | Example 20 |
|---|---|---|---|---|---|---|---|---|---|---|
| Stability evaluation test 2 | Upper part | Hue | 2.5Y to 7.5Y | 2.5Y to 7.5Y | 2.5Y to 7.5Y | 2.5Y to 7.5Y | 2.5Y to 7.5Y | 2.5Y to 7.5Y | 2.5Y to 7.5Y | 2.5Y to 7.5Y |
| | | Brightness | 9.0 | 9.0 | 9.0 | 9.0 | 9.0 | 9.0 | 9.0 | 9.0 |
| | | Saturation | 4.0 to 6.0 | 4.0 to 6.0 | 2.0 to 4.0 | 4.0 to 6.0 | 4.0 to 6.0 | 2.0 to 4.0 | 6.0 to 10.0 | 4.0 to 6.0 |
| | Middle part | Hue | 2.5Y to 7.5Y | 2.5Y to 7.5Y | 2.5Y to 7.5Y | 2.5Y to 7.5Y | 2.5Y to 7.5Y | 2.5Y to 7.5Y | 2.5Y to 7.5Y | 2.5Y to 7.5Y |
| | | Brightness | 9.0 | 9.0 | 9.0 | 9.0 | 9.0 | 9.0 | 9.0 | 9.0 |
| | | Saturation | 4.0 to 6.0 | 4.0 to 6.0 | 2.0 to 4.0 | 4.0 to 6.0 | 4.0 to 6.0 | 2.0 to 4.0 | 10.0 to 12.0 | 6.0 to 8.0 |
| | Lower part | Hue | 2.5Y to 7.5Y | 2.5Y to 7.5Y | 2.5Y to 7.5Y | 2.5Y to 7.5Y | 2.5Y to 7.5Y | 2.5Y to 7.5Y | 2.5Y to 7.5Y | 2.5Y to 7.5Y |
| | | Brightness | 9.0 | 9.0 | 9.0 | 9.0 | 9.0 | 9.0 | 9.0 | 9.0 |
| | | Saturation | 6.0 to 8.0 | 6.0 to 8.0 | 2.0 to 4.0 | 6.0 to 8.0 | 6.0 to 8.0 | 2.0 to 4.0 | 10.0 to 12.0 | 8.0 to 10.0 |

In Comparative Example 1, phase separation of the sample was confirmed, and, in the separated lower phases (lower part and middle part of the vial), the color turned dark yellow (hue 2.5Y to 7.5Y, brightness 9.0, saturation 10.0 to 12.0 in the Munsell color system). In addition, also in the upper phase (upper part of the vial), slight yellowing (hue 2.5Y to 7.5Y, brightness 9.0, saturation 6.0 to 10.0 in the Munsell color system) was confirmed.

In Examples 1, 8, 12, and 13, no phase separation was observed in the samples, but yellowing (hue 2.5Y to 7.5Y, brightness 9.0, saturation 6.0 to 8.0 in the Munsell color system) was confirmed in the lower part and slight yellowing was confirmed in the middle part and upper part (hue 2.5Y to 7.5Y, brightness 9.0, saturation 4.0 to 6.0 in the Munsell color system).

In Examples 9 and 17, no phase separation was observed in the samples, but slight yellowing (hue 2.5Y to 7.5Y, brightness 9.0, saturation 2.0 to 4.0 in the Munsell color system) was confirmed in the lower part, middle part, and upper part.

In Example 20, no phase separation was observed in the sample, but dark yellowing (hue 2.5Y to 7.5Y, brightness 9.0, saturation 8.0 to 10.0 in the Munsell color system) was confirmed in the lower part and yellowing (hue 2.5Y to 7.5Y, brightness 9.0, saturation 6.0 to 8.0 in the Munsell color system) was also seen in the middle part. In addition, a slight yellowing (hue 2.5Y to 7.5Y, brightness 9.0, saturation 4.0 to 6.0 in the Munsell color system) was confirmed in the upper part.

On the other hand, in Examples 2 to 7, 10, 11, 14 to 16, 18, 19, and 21 to 25, no phase separation or yellowing of the samples was seen and the milky white color was maintained.

It is considered that, when the emulsification of water-in-oil emulsion compositions collapses, aggregation, creaming, coalescence, and the like of the aqueous phase occurs and the aqueous phase accumulates at the bottom part of the sample. The aqueous phase in which ascorbyl magnesium phosphate is dissolved turns yellow after long-term, high-temperature storage. Accordingly, it is presumed that as the emulsion collapses, the lower part of the sample becomes a darker yellow color.

On the other hand, no separation of the samples was observed in Examples 1 to 25, where the viscosity was 9 Pa·s or higher, and no yellowing of the samples was observed in Examples 2 to 7, 10, 11, 14 to 16, 18, 19, and 21 to 25, where the viscosity was 14 Pa·s or higher. From the above, it is considered that the progression of separation and yellowing depends on the viscosity of the sample.

From the results of the stability evaluation tests 1 and 2, it was confirmed that crystal precipitation over time was suppressed in the water-in-oil emulsion compositions of Examples 1 to 25 and that yellowing was also further suppressed in the water-in-oil emulsion compositions of Examples 2 to 7, 10, 11, 14 to 16, 18, 19, and 21 to 25, which had excellent emulsion stability. In particular, it was shown that it is possible to suppress crystal precipitation over time even with a water-in-oil emulsion composition containing a high concentration of ascorbyl magnesium phosphate of 3% by mass or more.

From the above results, the present invention is able to provide a water-in-oil emulsion composition with excellent emulsion stability even when containing a high concentration of ascorbic acid phosphate ester and/or a salt thereof.

INDUSTRIAL APPLICABILITY

The present invention provides a water-in-oil emulsion composition containing ascorbic acid phosphate esters and/or salts thereof as active components, which is able to suppress crystal precipitation over time.

What is claimed is:

1. A water-in-oil emulsion composition comprising:
(a) at least one ascorbic acid phosphate ester compound selected from the group consisting of ascorbic acid phosphate esters and salts thereof;
(b) an organically modified clay mineral;
(c) an oil-based agent;
(d) water; and
(e) at least one thickening agent selected from the group consisting of natural polymers and cellulose-based polymers,
wherein
a content of the component (a) is 7% by mass to 20% by mass,
the component (b) is organically modified hectorite,
a content of the component (b) is 0.5% by mass to 1.5% by mass,
the component (e) is xanthan gum, gellan gum, or hydroxyethyl cellulose, and
a content of the component (e) is 0.08% by mass to 0.5% by mass when the component (e) is xanthan gum or gellan gum, and a content of the component (e) is 0.12% by mass to 0.5% by mass when the component (e) is hydroxyethyl cellulose.

2. The water-in-oil emulsion composition according to claim 1,
wherein the component (a) is a magnesium salt of the ascorbic acid phosphate ester.

3. The water-in-oil emulsion composition according to claim 1,
wherein the organically modified hectorite is disteardimonium hectorite or quaternium-18 hectorite.

4. The water-in-oil emulsion composition according to claim 1,
wherein a content of the component (d) is 50% by mass to 90% by mass.

5. The water-in-oil emulsion composition according to claim 1,
wherein a mass ratio of the component (c) to the component (d) is (c):(d)=1:2 to 1:10.

6. The water-in-oil emulsion composition according to claim 1,
wherein a viscosity measured at 25° C. is 9 Pa's to 50 Pa·s.

7. The water-in-oil emulsion composition according to claim 1, wherein the water-in-oil emulsion composition is a cosmetic.

8. The water-in-oil emulsion composition according to claim 1, wherein the component (c) comprises isodecyl neopentanoate.

9. The water-in-oil emulsion composition according to claim 1, wherein the component (c) comprises caprylyl laurate.

10. The water-in-oil emulsion composition according to claim 1, wherein the component (c) comprises caprylyl laurate, isodecyl neopentanoate, candlenut oil, and squalane.

* * * * *